(12) United States Patent
Park

(10) Patent No.: US 11,925,528 B1
(45) Date of Patent: Mar. 12, 2024

(54) SINUS LIFT BONE AUGMENTATION SURGICAL INSTRUMENTS AND METHODS

(71) Applicant: Joseph W. Park, Columbia, SC (US)

(72) Inventor: Joseph W. Park, Columbia, SC (US)

( * ) Notice: Subject to any disclaimer, the term of this patent is extended or adjusted under 35 U.S.C. 154(b) by 0 days.

(21) Appl. No.: 18/332,722

(22) Filed: Jun. 10, 2023

(51) Int. Cl.
*A61C 8/00* (2006.01)
*A61B 17/16* (2006.01)
*A61C 8/02* (2006.01)

(52) U.S. Cl.
CPC ........ *A61C 8/0092* (2013.01); *A61B 17/1617* (2013.01); *A61C 8/0006* (2013.01); *A61B 17/1688* (2013.01)

(58) Field of Classification Search
CPC .. A61C 8/0092; A61C 8/0006; A61B 17/1617
See application file for complete search history.

(56) References Cited

U.S. PATENT DOCUMENTS

| | | | | |
|---|---|---|---|---|
| 5,711,315 | A * | 1/1998 | Jerusalmy | A61B 90/00 433/167 |
| 5,899,696 | A * | 5/1999 | Shimoda | A61C 8/0092 433/172 |
| 7,125,253 | B2 * | 10/2006 | Kitamura | A61C 8/0092 433/167 |
| 7,510,397 | B2 * | 3/2009 | Hochman | A61C 8/0033 433/172 |
| 7,662,188 | B2 * | 2/2010 | Yamada | A61C 8/0089 433/172 |
| 7,837,707 | B2 * | 11/2010 | Yamada | A61C 8/0089 606/213 |
| 8,377,064 | B2 * | 2/2013 | Wallis | A61B 17/24 606/86 R |
| 2008/0161819 | A1 * | 7/2008 | Yamada | A61B 17/24 606/92 |
| 2009/0004624 | A1 * | 1/2009 | Lee | A61C 8/0006 433/144 |
| 2010/0291511 | A1 * | 11/2010 | Lee | A61C 8/0089 433/215 |
| 2011/0039232 | A1 * | 2/2011 | Yu | A61C 8/0092 433/173 |
| 2011/0117519 | A1 * | 5/2011 | Yamada | A61C 8/0092 433/141 |
| 2016/0228219 | A1 * | 8/2016 | Chu | A61C 8/0092 |

FOREIGN PATENT DOCUMENTS

DE 202010010118 * 11/2010

* cited by examiner

*Primary Examiner* — Ralph A Lewis
(74) *Attorney, Agent, or Firm* — Nelson Mullins Riley & Scarborough LLP

(57) ABSTRACT

A surgical instrument for use in a sinus lift procedure and methods for performing sinus lift procedures. A surgical instrument includes a shank having a body portion, a first end, an opposite second end, and a neck portion disposed between the body portion and the first end. The shank body portion defines a first longitudinal axis and the neck portion defines a second longitudinal axis. The shank further defines a head coupled with the first end. The head includes a flat proximal surface that extends radially outward of the neck portion and a domed distal surface opposite the first proximal surface. The second longitudinal axis is perpendicular to the proximal surface.

18 Claims, 9 Drawing Sheets

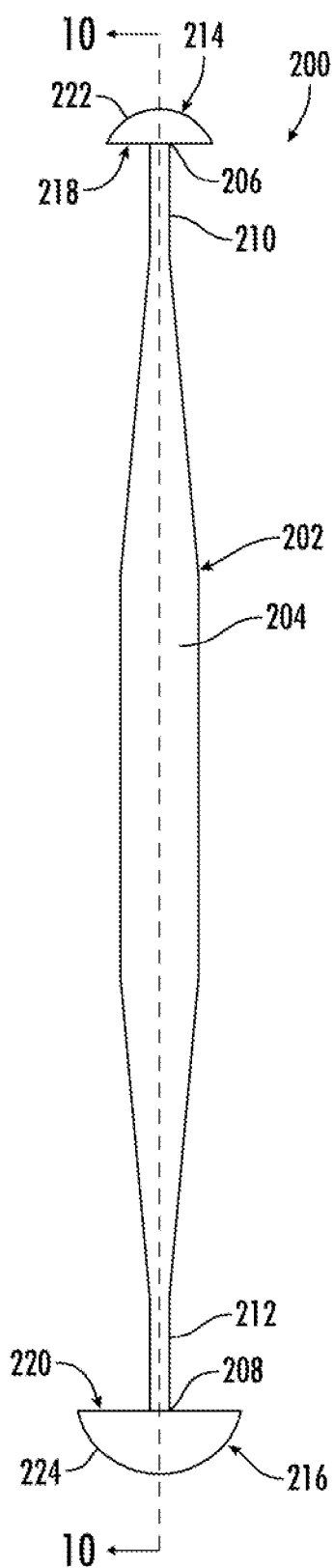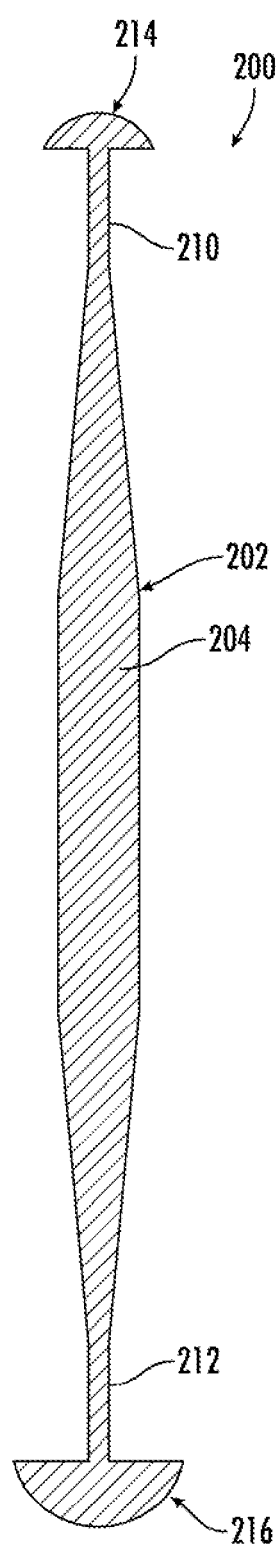
FIG. 9
FIG. 10

SINUS LIFT BONE AUGMENTATION SURGICAL INSTRUMENTS AND METHODS

TECHNICAL FIELD

Embodiments of the present invention generally relate to the field of oral and facial surgery and implements and surgical techniques used therein. More particularly, embodiments of the present invention relate to surgical instruments for laterally and superiorly spreading and compacting bone graft material under the sinus membrane once an indirect sinus lift procedure has been performed on a patient.

BACKGROUND

In the field of oral and facial surgery, dental implants are often used in the place of teeth that are lost. Dental implants are often secured into the maxillary bone at the location of a lost tooth, for example by screwing the implant into a bore or channel that is drilled into the maxillary bone at this location. However, dental implants require the maxillary bone to be thick enough at the site of the implant to support the implant in use. As used herein, and unless otherwise indicated by the context, the terms thick and thickness refer to both the inferior to superior anatomical direction (e.g., up and down vertically on the page) and to the lateral anatomical direction (e.g., into and out of the page). If the bone is not adequately available at the site of the implant, for example such that an upper portion of the implant is not surrounded by bone, this can lead to instability and failure of the implant. FIG. 1 shows the posterior maxillary bone 10 of a patient illustrating the site 20 of a lost tooth. The maxillary bone is not as thick at site 20 as it is in surrounding locations (e.g., due to resorption of bone following the loss of the tooth, pneumatization of the sinus, or just inadequate bone height in some patients). As a result, a floor 30 of the maxillary sinus 40 is low at site 20. Site 20 in this example would not be suitable for a dental implant until floor 30 is augmented, or lifted.

A number of surgical procedures are known for augmentation of the sinus floor 30 at the site of an implant, among others including the Tatum sinus lift procedure and the Summers technique. In these procedures and others, sinus floor augmentation is achieved through placement of bone graft material between the maxillary bone and the maxillary sinus (Schneiderian) membrane at the location of low thickness. Depending on the extent of augmentation needed, this can be done either at the time the implant is installed or in a first procedure that takes place several months prior to installation of the implant.

SUMMARY

In accordance with one embodiment, the present invention provides a surgical instrument for use in a sinus lift procedure. The surgical instrument comprises a shank having a body portion, a first end, an opposite second end, and a neck portion disposed between the body portion and the first end. The shank body portion defines a first longitudinal axis and the neck portion defines a second longitudinal axis. The shank further defines a head coupled with the first end. The head comprises a flat proximal surface that extends radially outward of the neck portion and a domed distal surface opposite the first proximal surface. The second longitudinal axis is perpendicular to the proximal surface.

In accordance with another embodiment, the present invention provides a method of performing a sinus lift procedure on a patient. The method comprises accessing the maxillary bone of the patient at a location for placement of a dental implant, defining a bore at the location beneath the patient's maxillary sinus, and fracturing the maxillary bone remaining at a distal end of the bore. The method also comprises elevating the Schneiderian membrane relative to an inferior surface of the maxillary sinus to define a pocket above the location and using a surgical instrument to push bone graft material into the pocket laterally and superiorly of the bore. The surgical instrument comprises a shank having a body portion, a first end, an opposite second end, and a first neck portion disposed between the body portion and the first end. The shank body portion defines a first longitudinal axis and the first neck portion defines a second longitudinal axis. The shank further defines a first head coupled with the first end. The first head comprises a flat first proximal surface that extends radially outward of the first neck portion; a domed first distal surface opposite the first proximal surface; and a curved peripheral surface extending between the first proximal surface and the first distal surface. The second longitudinal axis is perpendicular to the first proximal surface. Finally, the method comprises placing the dental implant at the location.

In accordance with another embodiment, the present invention provides a method of performing a sinus lift procedure on a patient. The method comprises accessing the maxillary bone of the patient at a location where a dental implant is to be installed; defining a bore at the location beneath the patient's maxillary sinus; and, using an osteotome, fracturing the maxillary bone remaining at a distal end of the bore. The method also comprises elevating the Schneiderian membrane relative to an inferior surface of the maxillary sinus to define a pocket above the location and, using a surgical instrument, pushing bone graft material into the pocket laterally and superiorly of the bore. The surgical instrument comprises a shank having a body portion, a first end, an opposite second end, and a neck portion disposed between the body portion and the first end. The neck portion has a circular cross-section defining a first radius, and the neck portion defines a longitudinal axis. The surgical instrument also comprises a head comprising a proximal surface having a circular cross-section defining a second radius that exceeds the first radius, a spheroid distal surface opposite the proximal surface, and a lateral surface extending between the proximal surface and the distal surface. The proximal surface is coupled with the neck portion and the longitudinal axis is perpendicular to the proximal surface.

In accordance with yet another embodiment, the present invention provides a method of performing a sinus lift procedure on a patient. The method comprising accessing the maxillary bone of the patient at a location; defining a bore at the location beneath the patient's maxillary sinus; and using an osteotome, fracturing the maxillary bone remaining at a distal end of the bore. Also, the method comprises elevating the Schneiderian membrane relative to an inferior surface of the maxillary sinus to define a pocket above the location and, using a surgical instrument, pushing bone graft material into the pocket laterally and superiorly of the bore. The surgical instrument comprises a shank having a body portion, a first end, an opposite second end, and a neck portion disposed between the body portion and the first end. The neck portion has a circular cross-section defining a first radius and the neck portion defines a first longitudinal axis. The surgical instrument also comprises a head comprising a proximal surface having a circular cross-section defining a second radius that exceeds the first radius and a spheroid distal surface opposite the proximal surface. The proximal surface is coupled with the neck portion and the first longitudinal axis is perpendicular to the proximal surface. The spheroid distal surface comprises at least one groove defined therein or at least one projection extending outwardly therefrom.

BRIEF DESCRIPTION OF THE DRAWINGS

Figure 1:
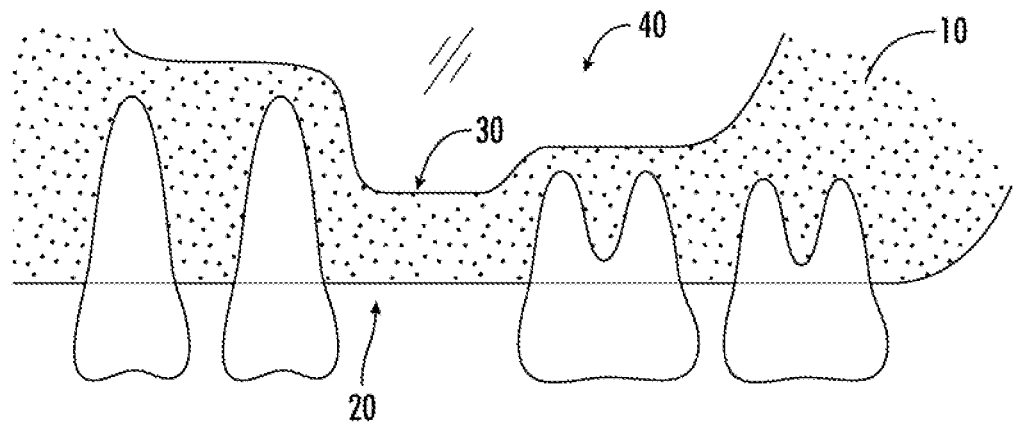
Figure 2:
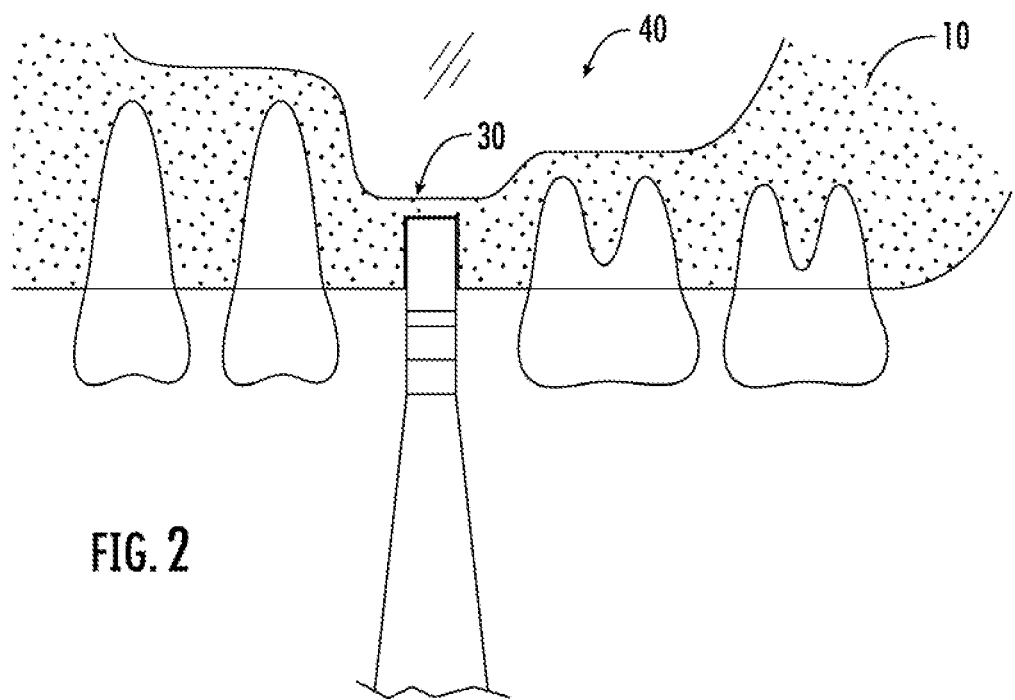
Figure 3:
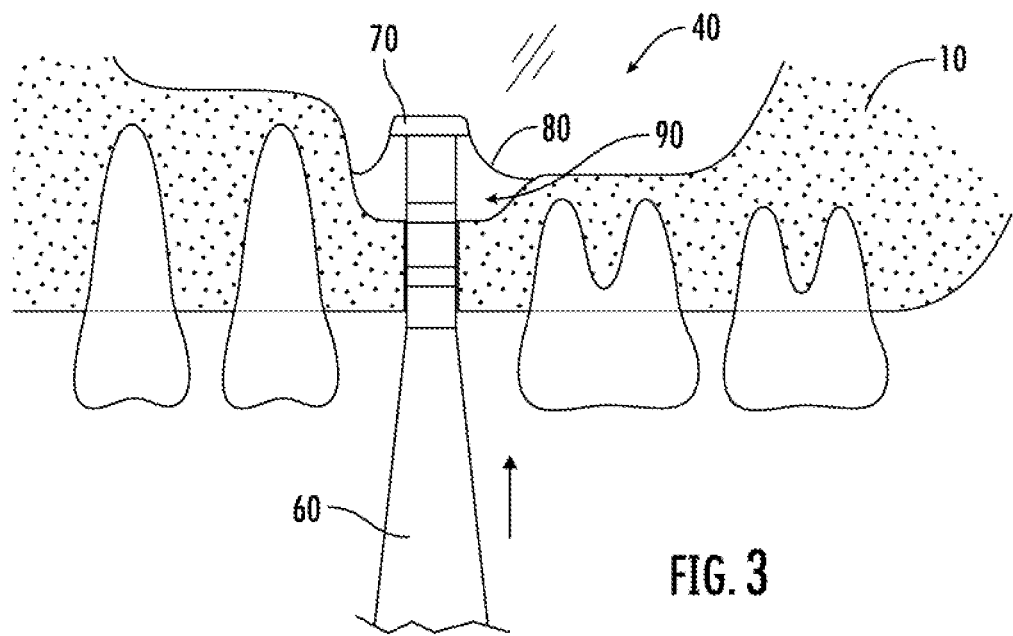
Figure 4:
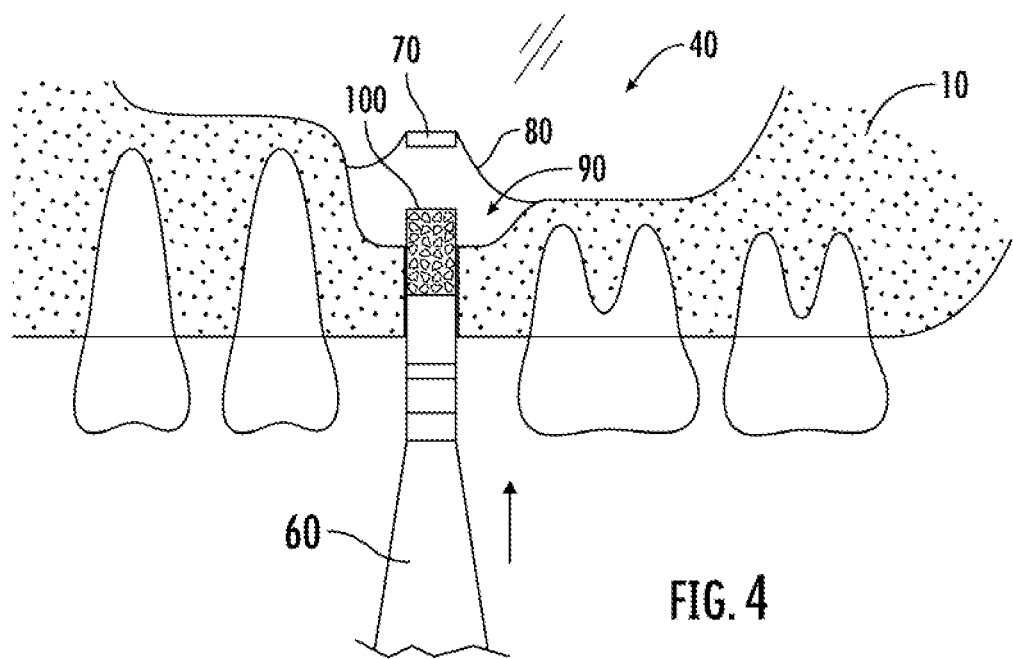
Figure 5:
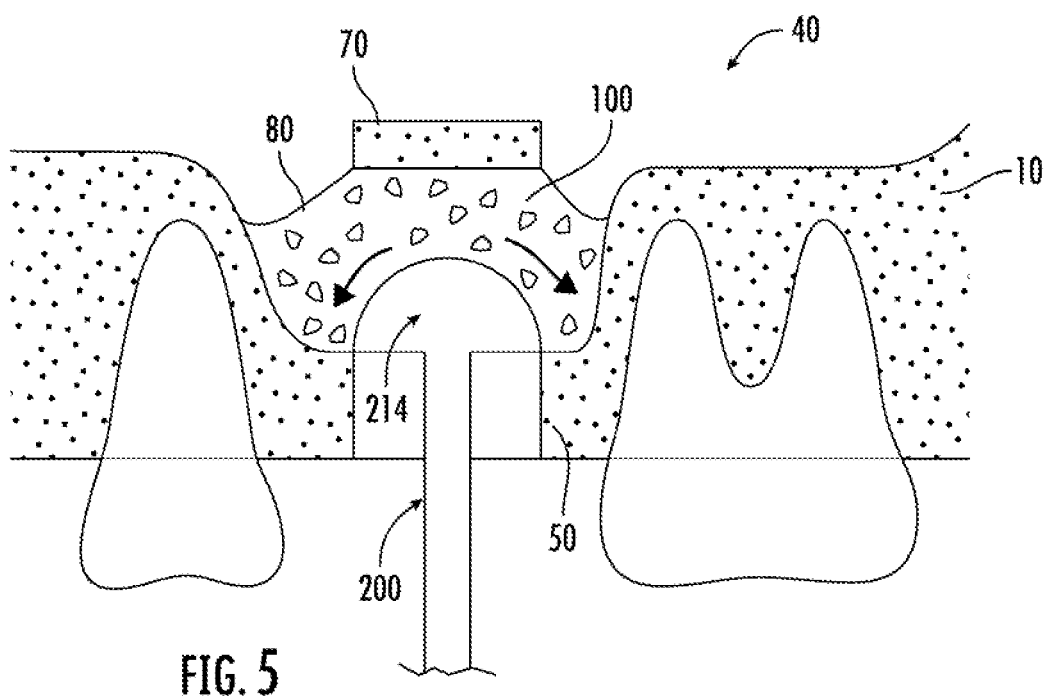
Figure 6:
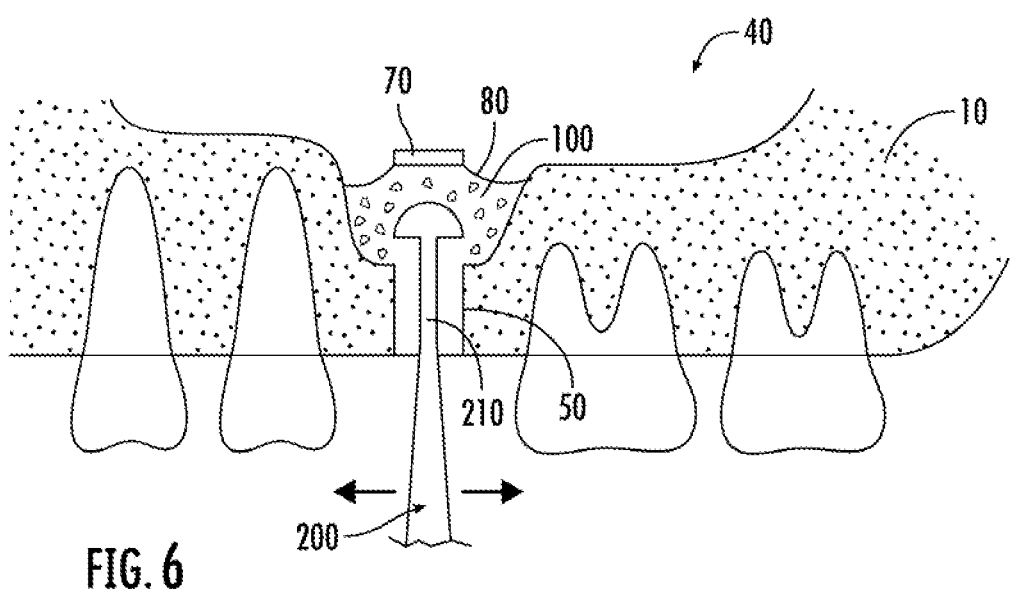
Figure 7:
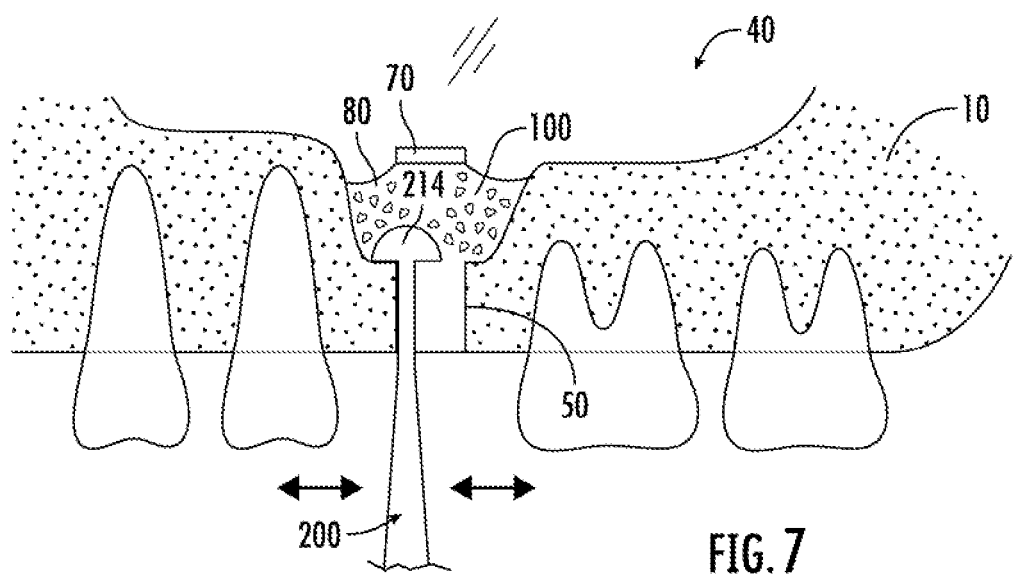
Figure 8:
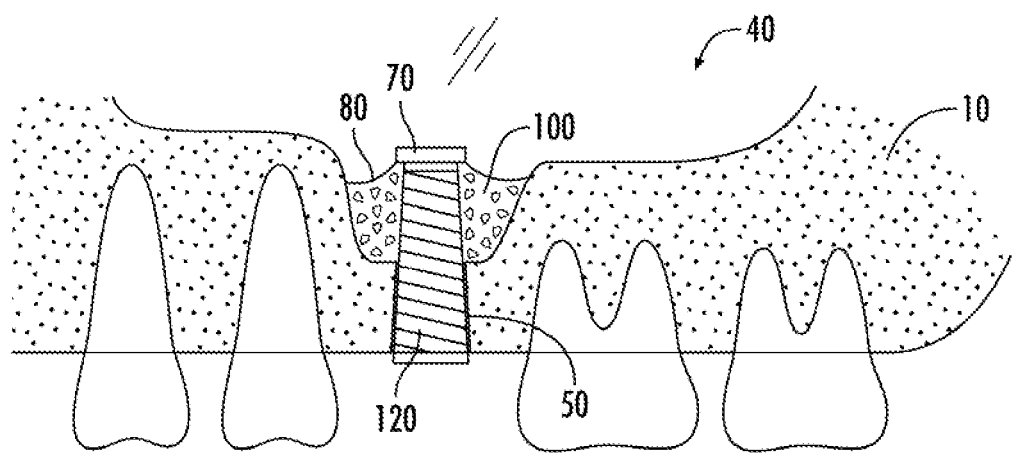
Figure 11:
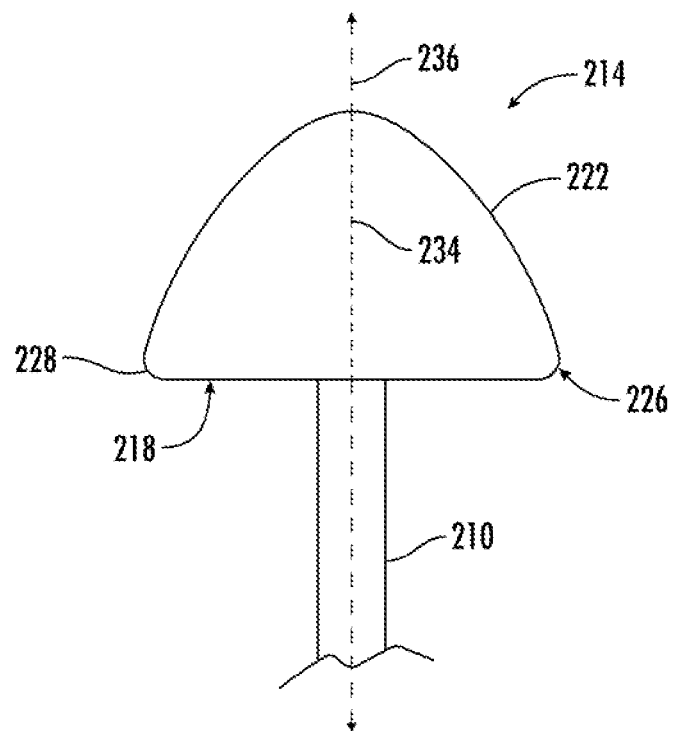
Figure 12:
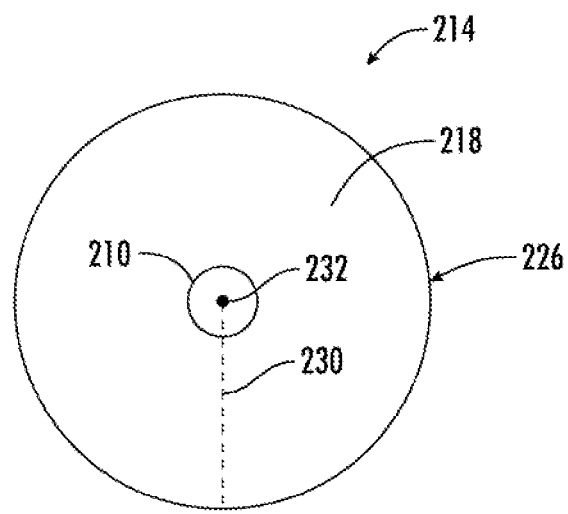
Figure 13:
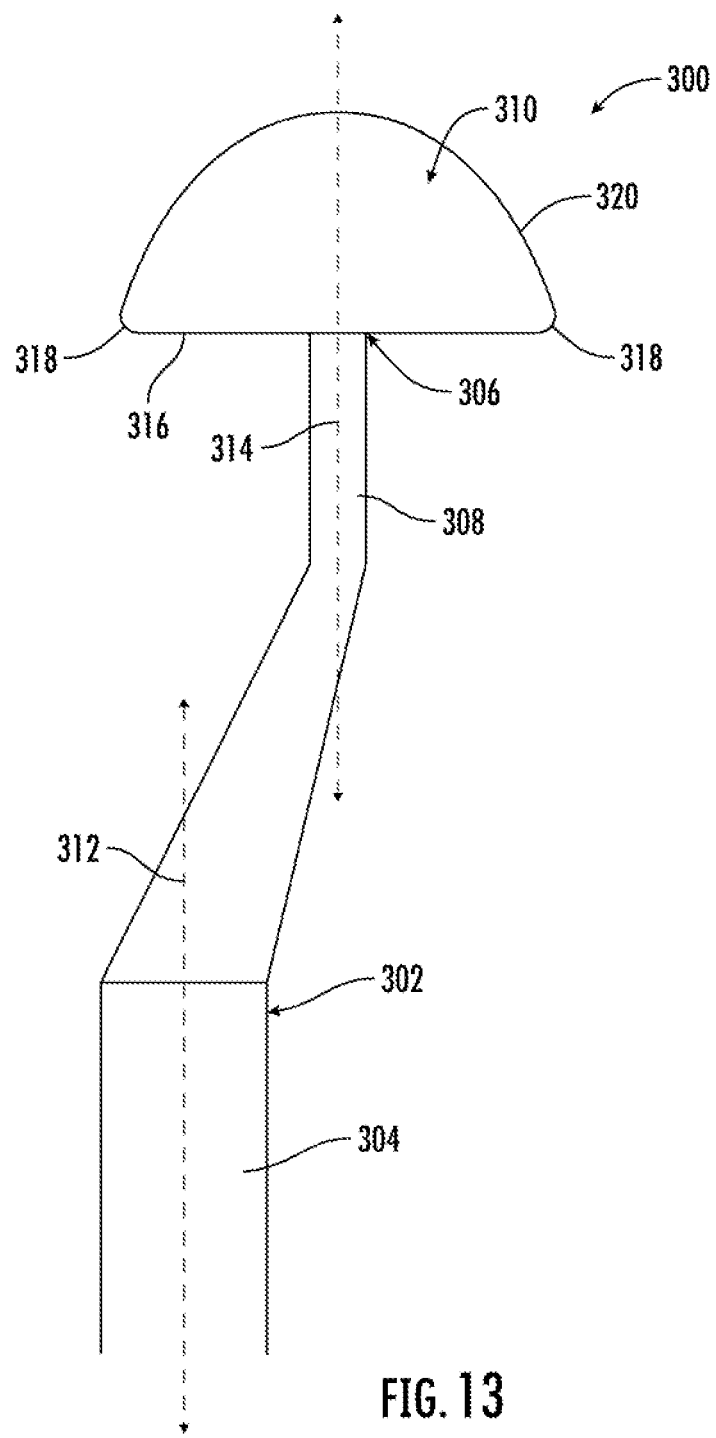
Figure 14:
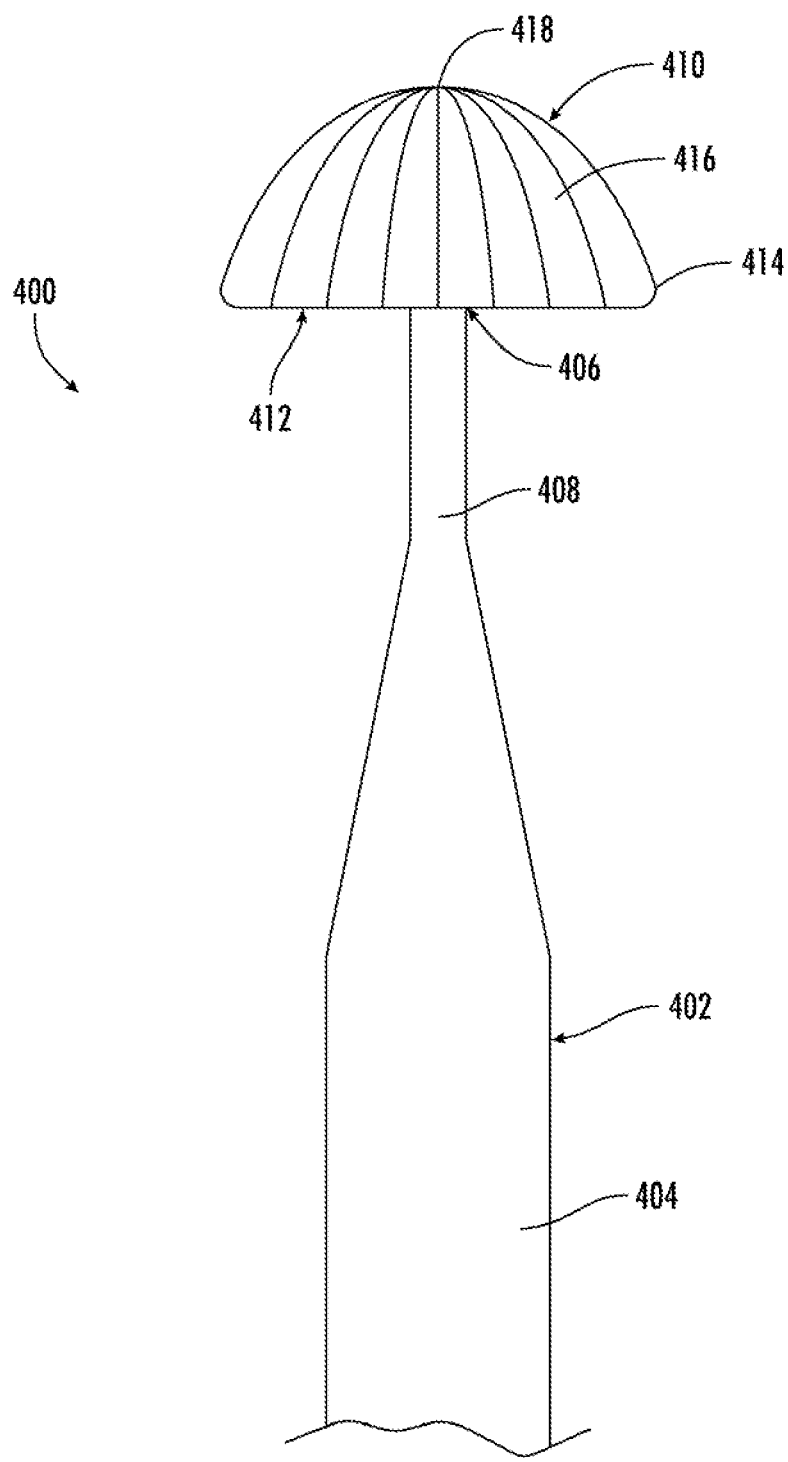
Figure 15:
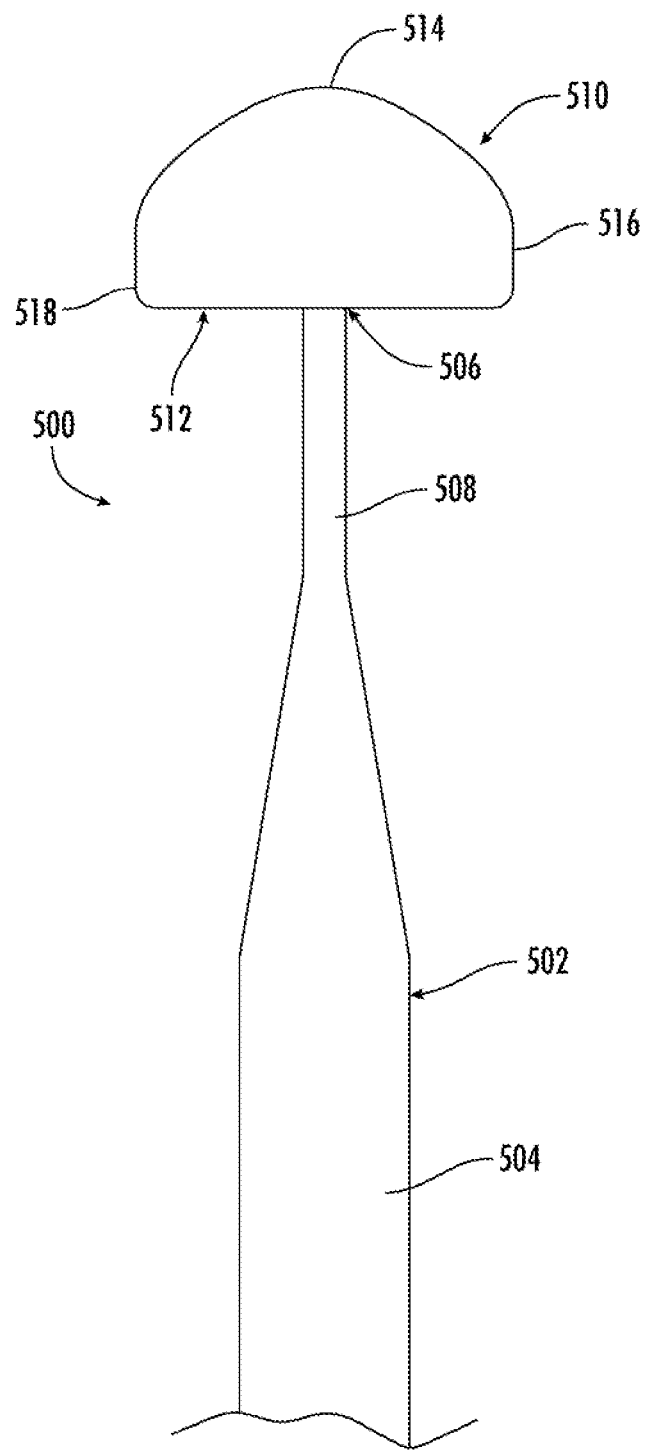

Having thus described some example embodiments in general terms, reference will now be made to the accompanying drawings, which are not necessarily drawn to scale, and wherein:

FIG. 1 is a schematic partial cross-sectional view of the posterior maxillary bone of a patient illustrating the site of a lost tooth and a low sinus floor;

FIG. 2 is a schematic partial cross-sectional view of the posterior maxillary bone of FIG. 1 after a drill has been used to create a hole in the maxillary bone at the site of the lost tooth and extending to a depth of 1-2 mm beneath the sinus floor, wherein an osteotome is inserted in the drilled hole;

FIG. 3 is a schematic partial cross-sectional view of the posterior maxillary bone of FIG. 2 after the osteotome has been used to fracture the remaining bone between the end of the hole and the sinus floor and push the fractured bone and sinus floor upward into the sinus, creating a pocket between the sinus floor and the posterior maxillary bone above the hole;

FIG. 4 is a schematic partial cross-sectional view of the posterior maxillary bone of FIG. 3 wherein an osteotome having a cylindrical rod is being used to push bone graft material into the pocket;

FIGS. 5-7 are schematic partial cross-sectional views of the posterior maxillary bone of FIG. 3 wherein an instrument in accordance with an embodiment of the present invention is being used to push bone graft material into the pocket laterally and superiorly;

FIG. 8 is a schematic partial cross-sectional view of the posterior maxillary bone of FIGS. after a dental implant has been placed in the hole, wherein bone graft material fills the pocket around the apex of the implant;

FIG. 9 is a schematic side elevation of a surgical instrument in accordance with an embodiment of the present invention;

FIG. 10 is a schematic cross-sectional view of the surgical instrument of FIG. 9 taken along the line 10-10 in FIG. 9;

FIG. 11 is an enlarged view of a head of a surgical instrument in accordance with an embodiment of the present invention;

FIG. 12 is a bottom side plan view of a head and corresponding neck portion of the surgical instrument of FIG. 9;

FIG. 13 is a schematic partial side elevation of a surgical instrument in accordance with another embodiment of the present invention;

FIG. 14 is a schematic partial side elevation of a surgical instrument in accordance with another embodiment of the present invention; and FIG. 15 is a schematic partial side elevation of a surgical instrument in accordance with another embodiment of the present invention.

Repeat use of reference characters in the present specification and drawings is intended to represent same or analogous features or elements of embodiments of the present invention.

DETAILED DESCRIPTION OF PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

As used herein, terms referring to a direction or a position relative to the orientation of a surgical instrument, such as but not limited to "vertical," "horizontal," "upper," "lower," "front," or "rear," refer to directions and relative positions with respect to the surgical instrument's orientation in its normal intended operation, as indicated in the Figures herein. Thus, for instance, the terms "vertical" and "upper" refer to the vertical direction and relative upper position in the perspectives of the Figures and should be understood in that context, even with respect to an apparatus that may be disposed in a different orientation. The term "substantially," as used herein, should be interpreted as "nearly" or "close to", such as to account for design and manufacturing tolerances of the apparatus.

Moreover, the term "or" as used in this application and the appended claims is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may. The phrase "at least one of A and B" is satisfied by any of A alone, B alone, A and B alone, and A and B with others. The phrase "one of A and B" is satisfied by A, whether or not also in the presence of B, and by B, whether or not also in the presence of A.

Embodiments of the present invention relate to improved surgical techniques for sinus lift procedures in connection with placement of dental implants and improved surgical instruments for inserting, spreading, and compacting bone graft material during a sinus lift procedure. Although one or more preferred embodiments are discussed herein in the context of a sinus lift procedure employing the Summers technique, those of skill in the art will appreciate that the present invention is not so limited. In particular, it is contemplated that embodiments of the present invention may be used with any sinus lift procedure where it is necessary to compress bone graft material laterally.

Turning to the Figures, those of skill in the art will appreciate that there are various scenarios in which clinicians perform sinus lift procedures. For example, after a tooth is extracted, the socket is oftentimes debrided and bone graft material is placed in the socket to rebuild the maxillary bone over a period of time (e.g., 4-6 months.) In one example, after the bone has regenerated, radiographic images are taken to assess the amount of bone available to place a dental implant in these sites. In many cases, due to pneumatization of the sinus, the amount of vertical bone is deficient and a sinus lift procedure is needed to provide the height of bone necessary to stabilize an implant. In another scenario, a clinician performs a sinus lift procedure right after a tooth is extracted. Again, the clinician will add bone graft material between the maxillary bone and the Schneiderian membrane. The implant is then placed either immediately thereafter or several months later, after the bone is first allowed to heal. Embodiments of the present invention can be used in any of these scenarios, among others.

In this regard, FIGS. 2-4 illustrate an example of a sinus lift procedure that can be modified in accordance with embodiments of the present invention. First, as shown in FIGS. 2-3, a clinician will use a drill to create a bore 50 at a depth in the maxillary bone 10 that is about 1-2 mm below the cortex of the sinus floor 30. The clinician then inserts an osteotome 60 into bore 50 and causes an upwardly-directed force to be applied thereto. This fractures the remaining bone at the upper end of bore 50, resulting in a bone segment 70. The clinician then uses the osteotome 60 to carefully lift the bone segment 70 and the Schneiderian (sinus) membrane 80 away from the maxillary floor 30. The clinician attempts to raise the sinus membrane 80 to a desired height for dental implant placement. Elevation of the Schneiderian membrane 80 results in a pocket 90 formed between the membrane 80 and the sinus floor 30.

In a typical procedure, and referring now also to FIG. 4, an osteotome, such as osteotome or another osteotome, is used to push bone graft material 100 into the osteotomy. Several loads of bone graft material may be loaded into the pocket 90 via bore 50 until completely filled. Once the clinician determines that membrane 80 has been lifted by a sufficient amount, the implant may be placed.

A drawback to this technique, however, is that the clinician is frequently unable to determine whether the bone graft material in pocket 90 has been sufficiently packed into the pocket and/or whether enough newly-added graft material is present in pocket 90 to create a sufficient buffer around the apex of the implant, once placed. As shown, for instance, the osteotome 60 used for this purpose in the example above has a cylindrical rod, and it does not move bone graft material laterally or pack it into place in pocket 90. Again, if not enough graft material is disposed around the implant's apex, then the bone may not grow there, the implant will not be stable, and it could fail. To the inventor's knowledge, there is no instrument to specifically push bone in lateral and superior directions to place the bone in the lifted sinus membrane area. Embodiments of the present invention solve this and other problems.

An embodiment of a surgical instrument 200 that can be used in performing a surgical procedure like that described above in connection with FIGS. 1-4 is shown schematically in FIGS. 9-10. FIGS. 9-10 are respective side elevation and cross-sectional view of surgical instrument 200. FIGS. 5-7 are schematic partial cross-sectional views of the posterior maxillary bone discussed above in connection with FIGS. 1-4, but in these figures surgical instrument 200 is being used to push bone graft material into the pocket laterally and superiorly. FIG. 8 is a schematic partial cross-sectional view of the posterior maxillary bone of FIGS. 5-7 after a dental implant 120 has been placed in bore 50.

More particularly, instrument 200 in this embodiment comprises a shank 202 comprising a body portion 204, a first end 206, and an opposite second end 208. The clinician may grasp the body portion 204 during use, and although the body portion 204 is illustrated as being a smooth cylindrical shape in this embodiment, those of skill in the art will appreciate that any suitable configuration may be used in other embodiments. For instance, body portion may have a gripping surface etched into it or may be covered with a gripping material in some embodiments. It also may define one or more protrusions of various shapes (e.g., annular, linear) to aid the clinician in gripping and manipulating instrument 200 during use.

A first neck portion 210 is disposed between body portion 204 and first end 206, and a second neck portion 212 is disposed between body portion 204 and second end 208. Shank 202 defines a first head 214 coupled with first end 206 and, in this embodiment, a second head 216 coupled with second end 208. Although instrument 200 has two heads 214 and 216 in this embodiment, in some embodiments, the shank 202 of instrument 200 may have only one head 214 or may have more than two heads. Where one head is provided, instrument 200 may not comprise neck portion 212. In one example embodiment, instrument 200 may be about 17 cm in length, but instrument 200 can be any suitable length in other embodiments.

In general, in the illustrated embodiment, heads 214 and 216 have proximal surfaces 218, 220, respectively, and rounded distal surfaces 222, 224, respectively. In this specific embodiment, proximal surfaces 218 and 220 are flat and, when viewed in plan, circular in shape. In other embodiments, either or both proximal surface 218 and/or 220 may have another suitable shape, such as elliptical, square, triangular, etc. Rounded distal surfaces 222, 224 are domed in this embodiment. In some embodiments, rounded distal surfaces 222, 224 are spherical caps or spherical domes, in that, for example, they can be or comprise a portion of a sphere cut off by a plane. In some embodiments, such a plane can pass through the center of the sphere, such that rounded distal surfaces 222, 224 are hemispherical in shape, but that is not the case in the embodiment of FIGS. 8-9. Proximal surfaces 218 and 220 extend radially outward of neck portions 210 and 212, respectively.

Neck portions 210 and 212 in this embodiment are circular in cross-section, but that is not required in all embodiments. In various embodiments, neck portions 210 and 212 are sized to have widths or diameters that are smaller than the diameters of the bores that are drilled for the implants with which heads 214 and 216, respectively, are intended to be used. In one embodiment, for example, either or both of neck portions 210 and/or 212 may have a width or diameter of about 1.5 mm. In one embodiment, neck portion 210 may be about 1.5 mm in width or diameter, and neck portion 212 may be about 2 mm in width or diameter. Further, neck portions 210 and 212 in this embodiment are smaller in diameter or width than body portion 204, although that is not required in all embodiments.

As discussed in more detail herein, however, proximal surfaces 218, 220 may not be entirely or perfectly flat in all embodiments, and many different types of rounded distal surfaces are contemplated and within the scope of the present invention. The rounded distal surfaces 222, 224 facilitate movement of bone graft material laterally and superiorly within a space formed between the maxillary bone and the sinus membrane in response to the clinician's movement of the surgical instrument 200 in a superior direction relative to the maxillary bone. The rounded distal surfaces 222, 224 also help compress and/or pack the bone graft material in the space.

In various embodiments, surgical instrument 200 may be formed of any material suitable for use in oral and facial surgical procedures. Thus, for instance, surgical instrument 200 preferably is formed of medical-grade stainless steel in some embodiments. This will allow for sterilization and make surgical instrument 200 non-rusting. In other embodiments, surgical instrument 200 can be formed of a medical-grade plastic material such as polycarbonate or ABS. As shown in FIG. 10, in the illustrated embodiment of surgical instrument 200, body portion 204, neck portions 210 and 212, and heads 214 and 216 are all integrally formed as a single instrument. Any suitable manufacturing technique for surgical instruments may be used to manufacture embodiments of instrument 200, such as casting, molding, threading, bonding, and/or welding. However, it is not required in all embodiments that the components of surgical instrument 200 be integrally formed. Indeed, in some embodiments, surgical instrument 200 may comprise a shank 202 (or only a body portion 204) that receives multiple removable head-and-neck portions. In other embodiments, only heads 214 and/or 216 may be removable. For instance, body portion 204 could define one or more threaded connections that allow a clinician to attach and remove heads analogous to heads 214 and/or 216 that have different sizes and/or shapes, as needed or desired for a particular patient or operation.

In some embodiments, heads 214 and 216 have different widths or diameters or shapes or sizes, for example to accommodate the placement of differently-sized dental implants. In other embodiments, heads 214 and 216 may be the same size or shape. In still other embodiments, heads 214 and 216 could have the same width or diameter but a differently curved or shaped distal surface, or vice versa. In the illustrated embodiment, head 214 is smaller in size than head 216.

Additional examples of heads 214 and 216 are provided with reference to FIG. 11, which is an enlarged view of a head 214 according to an embodiment of the invention, and FIG. 12, which is a bottom-side plan view of head 214 and neck portion 210 in the embodiment of FIG. 11. As shown, a peripheral surface 226 extends between proximal surface 218 and distal surface 222 in this embodiment. In some embodiments, peripheral surface 226 can be or comprise a peripheral edge of surface 218. In certain preferred embodiments, however, surface 218 may not define an edge, and peripheral surface 226 is a surface that, in cross section, defines a curve 228 extending between proximal surface 218 and distal surface 222. Where proximal surface 218 is circular in shape, the surface 226 that defines curve 228 may resemble the outer portion of a torus. In other embodiments, peripheral surface 226 may define other curves or shapes than that shown in FIG. 11. In certain embodiments, a dome-shaped head 214 has an edge that is smooth and non-cutting in order not to damage the sinus membrane.

In various embodiments, head 214 comprises or defines a radius 230 that extends from a center point 232 along proximal surface 218 (FIG. 12). Head 214 also comprises a second radius 234 (FIG. 11, shown as the shorter broken line) extending perpendicularly to the radius 230 and from the center point 232 to distal surface 222. In the illustrated embodiment, radius 234 is shorter than radius 230, but this is not required. In some embodiments, radii 230, 234 are the same length, and in some embodiments, radius 234 may be longer than radius 230. In one embodiment, radius 230 may be about 1.5 mm (e.g., the diameter of proximal surface may be about 3 mm), and radius 234 may be about 2 mm. In some embodiments, radius 234 may not be the same length at all points on distal surface 222. In yet other embodiments, and when viewed from a vertical cross-sectional plane passing through center point 232, the curvature of distal surface 222 may vary according to an equation defining a circle.

Although not shown, head 216 may define radii similar to radii 230, 234. In some embodiments, the radii of head 216 are proportionally smaller or larger than radii 230, 234. In other embodiments, the radii of head 216 have different proportions. In one example embodiment, the radius of proximal surface 220 can be about 2 mm, and the radius that extends perpendicularly from that radius and from the center point of proximal surface 220 to distal surface 224 can be about 3 mm.

Also as shown in FIG. 11, neck portion 210 defines a longitudinal axis 236 (shown as the longer broken line). In this embodiment, neck portion 210 is centered on proximal surface 218, and longitudinal axis 236 extends through center point 232. This is not required in all embodiments, and in certain embodiments, neck portion 210 need not be centered on proximal surface 218. The same is true of neck portion 212 and head 216 and its proximal surface 220. Also in this embodiment, longitudinal axis 236 is perpendicular to proximal surface 218, but again that is not required, and in some cases proximal surface 218 may be at a non-zero angle relative to longitudinal axis 236.

In use, and with reference to FIGS. 1-3 and 5-8, the clinician will first access the patient's maxillary bone 10 as described above and define a bore at the desired location to a depth that is between about 1 mm and 2 mm beneath the patient's maxillary sinus. In various embodiments, the diameter of bore 50 will vary depending on the size of the implant to be placed, but typically the diameter will be less than that of the implant. For example, for an implant with a 3.7 mm diameter, the bore 50 diameter may be about 3.2 mm. Likewise, for an implant with a 4.7 mm diameter, the bore 50 diameter may be about 4.2 mm. Using at least one osteotome, the clinician will then fracture the maxillary bone remaining at a distal end of the bore 50. Using the at least one osteotome, the clinician will then elevate the Schneiderian membrane 80 relative to the inferior surface of the maxillary sinus to define a pocket 90 above the location.

After the clinician has used the osteotome 60 to raise membrane 80 and define pocket 90, the clinician uses surgical instrument 200 to place bone graft material 100 rather than using an osteotome. In particular, in the illustrated embodiment, the clinician inserts bone graft material 100 into bore 50 using head 214 of instrument 200. In various embodiments, the width or diameter of the head of instrument 200 is selected to be slightly smaller than the diameter of bore 50. In an embodiment of instrument 200 having two heads, one head may be 3 mm in diameter for use in placing implants with a 3.7 mm diameter, and the other head may be 4 mm in diameter for use in placing implants with a 4.7 mm diameter. Moreover, as noted herein, a kit according to an embodiment of the present invention could contain other instruments 200 with a head or heads sized for placement of dental implants having other diameters, such as 5 or 6 mm, among others.

In particular, the clinician applies force to instrument 200 in a superior direction, causing head 214 to move upward. As indicated by the arrows in FIG. 5, upward movement of head 214 causes bone graft material 100 to move laterally within pocket 90. Also, as shown by the arrows in FIGS. 6-7, and because neck portion 210 is smaller in width or diameter than the diameter of bore 50, the clinician is able to move surgical instrument 200 and its head 214 laterally within bore 50. This allows the clinician to compress the bone graft material 100 in pocket 90. For instance, as shown in FIG. 7, the clinician is able to move neck portion 210 into engagement with the wall of bore 50. Because of the 90 degree (in this embodiment) "cut back" defined by proximal surface 218 and neck portion 210 relative to the upper surface of head 214, a portion of head 214 is disposed in pocket 90 when neck portion 210 is in this position. As a result, head 214 can be used to further compress bone graft material 100 laterally within pocket 90. The clinician may do this on all sides of bore 50 (e.g., by moving surgical instrument in a circular motion within bore 50). In some embodiments, the clinician may also rotate instrument 200 in place to compress bone graft material 100. As noted above, typically the clinician will insert multiple plugs of bone graft material 100, until pocket 90 is filled and the bone graft material 90 is spread and compressed laterally and superiorly.

Due to the rounded distal surface of head 214, the clinician is unlikely to damage the site (including membrane 80) in this process. This is particularly important in cases where the sinus floor is also angled or at a slope, where it is easy for prior art osteotomes to tear the very thin Schneiderian membrane. Again, traditional osteotomes have an edge that is more likely to lead to a tear. In various embodiments, the rounded shapes and dimensions of heads 214 and 216 also are in contrast to an osteotome that might have a small ball point that is no larger than the diameter of the cylindrical osteotome described above. In this regard, the latter apply a pin point concentrated force that is more likely to injure the Schneiderian membrane, whereas embodiments of the present invention apply force over a much larger surface area. In one embodiment where the rounded distal surface 222 is hemispherical in shape with a radius of 3 mm, the total surface area may be about 56 mm^2. In various embodiments, the total surface area of a head's distal surface may be between about 25 mm^2 and 226 mm^2. In certain embodiments, the total surface area of a head's distal surface may be between about 50 mm^2 and 100 mm^2. Of course, where rounded distal surface 222 is not hemispherical in shape, or where the distal surface 222 is not continuous or smooth, the surface area may be larger or smaller.

Finally, as shown in FIG. 8, in some embodiments an implant is placed immediately after the pocket 90 is sufficiently filled with bone graft material. In that case, the clinician may screw an implant 120 into place in the maxillary bone via bore 50. More specifically, once the bone graft material is placed, the dental implant 120 is inserted in the osteotomy site to desired height and diameter to provide stable initial rigidity. However, as noted above, another scenario may involve elevating the sinus membrane after an extraction and using the surgical instrument 200 to place the bone graft material 100 in the sinus lift area 90, but not placing the implant 120 simultaneously. This would allow the bone to heal first, before placing the implant 120 in the missing tooth site.

FIG. 13 is a schematic partial side elevation of a surgical instrument 300 in accordance with another embodiment of the present invention. Surgical instrument 300 is in many respects similar to surgical instrument 200, described above. Thus, it comprises a shank 302 comprising a body portion 304 having a first end 306. Shank 302 also comprises a neck portion 308, and a head 310 is coupled with first end 306.

In the embodiment of FIG. 13, however, body portion 304 defines a longitudinal axis 312, and neck portion 308 defines a longitudinal axis 314, and longitudinal axes 312 and 314 are parallel but offset from one another. This is in contrast to the embodiment of surgical instrument 200, wherein the longitudinal axis of body portion 204 was collinear with the longitudinal axis 236 of neck portion 210.

Additionally, head 310 defines a proximal surface 316 that is circular when viewed in plan. A curved peripheral surface 318 extends between proximal surface 316 and rounded distal surface 320. In this embodiment, the rounded distal surface 320 defines a curvature that varies relative to the proximal surface 316 according to a parabolic function. In other words, the curvature of distal surface 320 viewed along a cross-sectional plane is a parabolic curvature relative to an axis along the proximal surface 316.

Of course, surgical instruments in accordance with other embodiments of the present invention may have rounded heads having other curvatures. In some embodiments, for example, a head of a surgical instrument can be hemispherical in shape. In other words, the vertically- and horizontally-extending radii from the center point of proximal surface 316 would be the same length in such an embodiment. In still other embodiments, a head of a surgical instrument could comprise a distal surface that is ellipsoidal in shape, or it could comprise a portion or hemisphere of an oblate or prolate spheroid. All such configurations, among others, are within the scope of the present invention.

FIG. 14 is a schematic partial side elevation of a surgical instrument 400 in accordance with another embodiment of the present invention. Surgical instrument 400 is in many respects similar to surgical instruments 200 and 300, described above. Thus, it comprises a shank 402 comprising a body portion 404 having a first end 406. Shank 402 also comprises a neck portion 408, and a head 410 is coupled with first end 406. Additionally, head 410 defines a proximal surface 412 that is circular when viewed in plan. A curved peripheral surface 414 extends between proximal surface 412 and a rounded distal surface 416.

In the embodiment of FIG. 14, however, head 410 comprises a plurality of grooves 412 that in this case extend from a top center point 418 of distal surface 416 toward peripheral surface 414 and proximal surface 412. In the illustrated embodiment, grooves 412 are longitudinal and equally-spaced, and each may lie on a plane that extends perpendicularly to proximal surface 412. but that is not required in all embodiments. In various embodiments, any number of grooves 412 may be provided, including a single groove, and they need not extend from top center point 418. In some embodiments, for example, grooves 412 could lie on planes that are at an acute angle relative to proximal surface 412. In some embodiments, one or more grooves 412 may form a spiral on distal surface 416. Further, in some embodiments, rather than grooves 412 being defined in distal surface 416, one or more projections may be disposed on surface 416 in locations analogous to those just described. As those of skill in the art will appreciate, grooves 412 (or analogous projections) may help the clinician move bone graft material laterally and superiorly within a space formed between the maxillary bone and the sinus membrane and/or to compress the bone graft material in the space.

FIG. 15 is a schematic partial side elevation of a surgical instrument 500 in accordance with another embodiment of the present invention. Surgical instrument 500 is in many respects similar to surgical instruments 200, 300, and 400, described above. Thus, it comprises a shank 502 comprising a body portion 504 having a first end 506. Shank 502 also comprises a neck portion 508, and a head 510 is coupled with first end 506. Additionally, head 510 defines a proximal surface 512 that is circular when viewed in plan, and a rounded distal surface 514 that is opposite proximal surface 512.

In this embodiment, head 510 comprises a lateral surface 516 that depends from distal surface 514. A curved peripheral surface 518 extends between proximal surface 512 and lateral surface 516. In various embodiments, lateral surface 516 may have a shape that corresponds to the shape of peripheral surface 512. Thus, in this embodiment, lateral surface 516 may be cylindrical, though in other embodiments other shapes could be used. Here, lateral surface 516 depends vertically from distal surface 514 (e.g., at a right angle to proximal surface 512), but lateral surface 516 may also be sloped or angled in some embodiments, such that lateral surface 516 is frustoconical in shape. In various embodiments, the "height" or "length" of lateral surface 516 (e.g., the distance that lateral surface 516 extends between peripheral surface 518 and distal surface 514) may have any suitable dimension. In some embodiments, lateral surface 516 may be about to about 2 mm in height or length. In some embodiments, lateral surface 516 can have a height or length that is about the same as the radius of proximal surface 512.

Based on the foregoing, it will be appreciated that embodiments of the invention provide improved surgical techniques for sinus lift procedures in connection with placement of dental implants and improved surgical instruments for inserting, spreading, and compacting bone graft material during a sinus lift procedure. Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A method of performing a sinus lift procedure on a patient, the method comprising:
   accessing the maxillary bone of the patient at a location for placement of a dental implant;
   defining a bore at the location beneath the patient's maxillary sinus;
   fracturing the maxillary bone remaining at a distal end of the bore;
   elevating the Schneiderian membrane relative to an inferior surface of the maxillary sinus to define a pocket above the location;
   using a surgical instrument, pushing bone graft material into the pocket laterally and superiorly of the bore;
   wherein the surgical instrument comprises:
   a shank having a body portion, a first end, an opposite second end, and a first neck portion disposed between the body portion and the first end, wherein the shank body portion defines a first longitudinal axis and the first neck portion defines a second longitudinal axis;
   the shank further defining a first head coupled with the first end;
   the first head comprising:
   a flat first proximal surface that extends radially outward of the first neck portion, wherein the first proximal surface is circular in shape;
   a domed first distal surface opposite the first proximal surface; and
   a curved peripheral surface extending between the first proximal surface and the first distal surface;
   wherein the second longitudinal axis is perpendicular to the first proximal surface and extends through a central point of the first proximal surface; and
   placing the dental implant at the location.

2. The method of claim 1, wherein the first neck portion defines a smaller diameter or width than the diameter or width of the body portion.

3. The method of claim 1, wherein the domed first distal surface is hemispherical in shape.

4. The method of claim 1, further comprising a second neck portion disposed between the body portion and the second end and a second head coupled with the second end.

5. The method of claim 4, wherein the second head comprises a flat second proximal surface that extends radially outward of the second neck portion and a domed second distal surface opposite the second proximal surface.

6. The method of claim 5, wherein the first proximal surface defines a first radius extending along the first proximal surface, wherein the first head comprises a second radius extending perpendicularly to the first radius between the first proximal surface and the domed first distal surface, wherein the second proximal surface defines a third radius extending along the second proximal surface, wherein the second head comprises a fourth radius extending perpendicularly to the third radius between the second proximal surface and the domed second distal surface, wherein the first radius is smaller than the third radius, and wherein the second radius is smaller than the fourth radius.

7. The method of claim 6, wherein the first radius is shorter than the second radius.

8. The method of claim 1, wherein the first and second longitudinal axes are collinear.

9. The method of claim 1, wherein the domed distal surface has a curvature that varies relative to the proximal surface according to a parabolic function.

10. A method of performing a sinus lift procedure on a patient, the method comprising:
    accessing the maxillary bone of the patient at a location where a dental implant is to be installed;
    defining a bore at the location beneath the patient's maxillary sinus;
    using an osteotome, fracturing the maxillary bone remaining at a distal end of the bore;
    elevating the Schneiderian membrane relative to an inferior surface of the maxillary sinus to define a pocket above the location;
    using a surgical instrument, pushing bone graft material into the pocket laterally and superiorly of the bore;
    wherein the surgical instrument comprises:
    a shank having a body portion, a first end, an opposite second end, and a neck portion disposed between the body portion and the first end, wherein the neck portion has a circular cross-section defining a first radius and wherein the neck portion defines a longitudinal axis;

a head, comprising:
  a flat circular proximal surface defining a second radius that exceeds the first radius, wherein the proximal surface is coupled with the neck portion and wherein the longitudinal axis is perpendicular to the proximal surface and extends through a central portion of the proximal surface;
  a spheroid distal surface opposite the proximal surface; and
  a lateral surface extending between the proximal surface and the distal surface.

11. The method of claim 10, wherein the lateral surface is disposed at a periphery of the proximal surface.

12. The method of claim 10, wherein the distal surface is shaped as an oblate spheroid.

13. The method of claim 10, wherein the second radius is at least twice as large as the first radius.

14. The method of claim 10, wherein the bore is drilled to depth that is between about 1 mm and 2 mm beneath the patient's maxillary sinus.

15. A method of performing a sinus lift procedure on a patient, the method comprising:
  accessing the maxillary bone of the patient at a location;
  defining a bore at the location beneath the patient's maxillary sinus;
  using an osteotome, fracturing the maxillary bone remaining at a distal end of the bore;
  elevating the Schneiderian membrane relative to an inferior surface of the maxillary sinus to define a pocket above the location;
  using a surgical instrument, pushing bone graft material into the pocket laterally and superiorly of the bore;
  wherein the surgical instrument comprises:
    a shank having a body portion, a first end, an opposite second end, and a neck portion disposed between the body portion and the first end, wherein the neck portion has a circular cross-section defining a first radius and wherein the neck portion defines a first longitudinal axis;
    a head, comprising:
      a proximal surface having a circular cross-section defining a second radius that exceeds the first radius, wherein the proximal surface is coupled with the neck portion and wherein the first longitudinal axis is perpendicular to the proximal surface;
      a spheroid distal surface opposite the proximal surface, the spheroid distal surface comprising at least one groove defined therein or at least one projection extending outwardly therefrom.

16. The method of claim 15, further comprising a lateral surface extending between the proximal surface and the distal surface.

17. The method of claim 16, wherein the lateral surface is cylindrical in shape and defines a second longitudinal axis that is parallel with the first longitudinal axis.

18. The method of claim 15, wherein the distal surface defines a plurality of grooves that are longitudinal, and wherein each of the plurality of grooves lies on a respective plane that extends perpendicularly to the proximal surface.

* * * * *